United States Patent
Lohman

(10) Patent No.: US 9,465,918 B1
(45) Date of Patent: Oct. 11, 2016

(54) ELECTRONIC DRUG DISPENSER SYSTEM

(71) Applicant: Cheryl Lohman, Germantown, MD (US)

(72) Inventor: Cheryl Lohman, Germantown, MD (US)

(*) Notice: Subject to any disclaimer, the term of this patent is extended or adjusted under 35 U.S.C. 154(b) by 0 days.

(21) Appl. No.: 14/947,721

(22) Filed: Nov. 20, 2015

(51) Int. Cl.
*G05B 13/02* (2006.01)
*G06F 19/00* (2011.01)
*A61B 5/117* (2016.01)
*A61J 7/00* (2006.01)
*G07C 9/00* (2006.01)
*G06F 3/041* (2006.01)
*G06F 21/32* (2013.01)
*G06Q 50/22* (2012.01)

(52) U.S. Cl.
CPC ......... *G06F 19/3462* (2013.01); *A61B 5/1172* (2013.01); *A61J 7/0076* (2013.01); *A61J 7/0084* (2013.01); *G06F 3/041* (2013.01); *G06F 19/363* (2013.01); *G06F 21/32* (2013.01); *G06Q 50/22* (2013.01); *G07C 9/00158* (2013.01); *G07C 9/00563* (2013.01)

(58) Field of Classification Search
CPC .. G06F 19/3462; G06F 3/041; G06F 19/363; G06F 21/32; A61B 5/1172; A61J 7/0076; A61J 7/0084; G06Q 50/22; G07C 9/00158; G07C 9/00563
USPC ........................................................ 340/5.53
See application file for complete search history.

(56) References Cited

U.S. PATENT DOCUMENTS

| | | | | |
|---|---|---|---|---|
| 2003/0052787 A1* | 3/2003 | Zerhusen | ............. | A47B 23/046 340/573.1 |
| 2005/0125255 A1* | 6/2005 | Mockett | ................. | F16M 11/04 705/2 |
| 2012/0253837 A1* | 10/2012 | Cashman | ............... | H04N 7/141 705/2 |
| 2012/0316405 A1* | 12/2012 | Taylor | .................... | G06Q 50/24 600/301 |
| 2015/0251839 A1* | 9/2015 | Denny | .................... | B65D 83/02 340/686.6 |

FOREIGN PATENT DOCUMENTS

WO    WO 2013/033033 A1    8/2012
WO    WO 2013033033 A1 *  3/2013  ............ A61J 7/0084

* cited by examiner

*Primary Examiner* — Edwin Holloway, III
(74) *Attorney, Agent, or Firm* — Michael L. Greenberg, Esq.; Greenberg & Lieberman, LLC

(57) ABSTRACT

A medication administration and tracking system is described. The system is equipped with an electric medication dispenser configured to administer medication to a patient in a hospital bed without intervention from hospital staff. The dispenser is configured to allocate safe doses of prescribed or over-the-counter medications to a patient upon request by the patient. At least one method of biometric authentication is employed to solely permit access to the medication to the patient upon confirmation of his or her identity. A camera disposed on the dispenser is configured to witness the patient take the medication, and track the time and date of consumption. The medications administered are preferably equipped with a tracking sensor to help track medication levels within the patient, and monitor treatment efficacy.

6 Claims, 3 Drawing Sheets

Medical Intake Questionnaire
[Medical Facility Name]

Name: _____  Present Date: _____
Address: _____  Date of Birth: _____
_____  Medical Record No: ____

1. Do you take any medication for anxiety?  Y  N
   _____

2. Do you take medication to assist with
   bowel movements?  Y  N
   _____

3. Do you ever use an inhaler?  Y  N
   _____

4. Do you use Opiods?  Y  N
   If so, when was your last dose? _____
5. When was your last alcoholic drink? _____

6. Do you experience pain?  Y  N
       Lower Back Pain?  Y  N
       Knee or Hip Pain?  Y  N
       Headache?  Y  N
       Shoulder Immbobility?  Y  N 7. Do you smoke?  Y  N 8. Are you presently using Nicotine  Y  N
   Replacement Treatments (NRT)?
9. Have you had Cirrhosis?  Y  N
   Liver failure?  Or  Kidney failure?
10. Do you take any medications to help
    you sleep? _____  Y  N 11. Can you use your hands to pick up pills?  Y  N 12. Could you be pregnant?  Y  N

60

FIG. 2

ELECTRONIC DRUG DISPENSER SYSTEM

FIELD OF THE PRESENT INVENTION

The present invention relates generally to regulated patient drug administration, and more specifically relates to a system for administering drugs to patients via a biometrically authenticated electronic drug dispensing system configured to enable patients to self-administer medications while in a hospital bed without nurse assistance.

BACKGROUND OF THE PRESENT INVENTION

Elderly or ill patients admitted to the hospital are often prescribed medications to help alleviate pain, expedite recovery, stabilize conditions, and otherwise bring comfort to the patient during his or her stay. Conventionally, patients admitted into hospitals are not allowed to self-administer medications, including over-the-counter painkillers, as each dose of medication must be approved by the patient's physician prior to administration.

As a result, many patients are often left waiting for approval before they are allowed to take their medications in a timely fashion. Additionally, it is customary for a nurse to bring the prescribed or requested medications to the patient after approval at the appropriate time windows. This often takes a good deal of time, and as such, pain control in hospitals is regarded as slow at best.

Many patients come to the conclusion that they could have simply brought medication from home, such as Tylenol™ or Ibuprofen, and alleviated their pain much faster than through the proper channels at the hospital. Additionally, it is cheaper to bring medication from home. Unfortunately, doctors and hospital staff frown upon this, and attempt to prohibit the behavior, as each medication ingested by the patient must be tracked and monitored. If medications are not carefully tracked, unknown medications can cause serious interactions with new medications. New medications may need to be adjusted for patient-specific factors.

Thus, there is a need for a system for the self-administration of medications to a patient in a hospital bed that allows the patient to independently administer prescription and over-the-counter medication at the correct times and doses without nurse intervention. Such a system preferably tracks when medication is dispensed, and employs a camera (and/or other identity authentication technology) to verify the medication is dispensed to the correct patient, and that the patient consumes the medication when dispensed. Such a system is also preferably configured to function in tandem with existing digital health technologies such as Proteus™ by Proteus Digital Health™ to further authenticate administration of the medication. This system is preferably capable of saving hospitals and other health centers money by lessening nursing interruptions and decreasing errors, which can be better spent on patient care.

A reference is made in the prior art to a similar apparatus. International Publication Number WO 2013/033033 A1, filed on Aug. 27, 2012 by Kraft et al. is for a Portable Drug Dispenser. Kraft et al. teaches a portable device configured to dispense personal medication that is equipped with biometric authentication and network interactivity. However, the device taught by Kraft et al. is designed for portable use rather than use in a hospital by patients for convenience and to expedite pain relief as is the intent of the present invention.

SUMMARY OF THE PRESENT INVENTION

The present invention is an electronic drug dispenser system configured to be fixed at a bedside of a patient in a hospital. The system of the present invention employs biometric authentication to verify the identity of the patient accessing the dispenser. The biometric authentication preferably employs the fingerprint, thumb-impression, iris scan, face recognition, and/or voice identification to verify the identity of the patient. The system of the present invention is designed such that a patient may personally take the medicine from the dispenser without a need to call a nurse, and self-administer the medication. The system also is equipped with a camera configured to track the patient accessing the dispenser while taking the medications. An alternate power back-up is also preferably provided by the system for use in case of power failure. Additionally, the present invention is preferably configured to continue operation independently without a network connection in the event that the network goes down.

Additionally, the system of the present invention also preferably performs drug tracking in order to confirm the ingestion of the drug by the patient for keeping a record of the medication provided to the patient. As such, the medications dispensed via the system of the present invention preferably include medication ingestion tracking technology, such as that employed by Proteus Digital Health. The system of the present invention may be configured to function in tandem with the medication tracking system of Proteus Digital Health.

BRIEF DESCRIPTION OF THE DRAWINGS

The present invention will be better understood with reference to the appended drawing sheets, wherein:

FIG. 2 is an example embodiment of the intake questionnaire preferably administered during a patient's admission to the hospital or medical institution that facilitates safe use of the process of the present invention.

DETAILED DESCRIPTION OF THE PREFERRED EMBODIMENT

Figure 1:
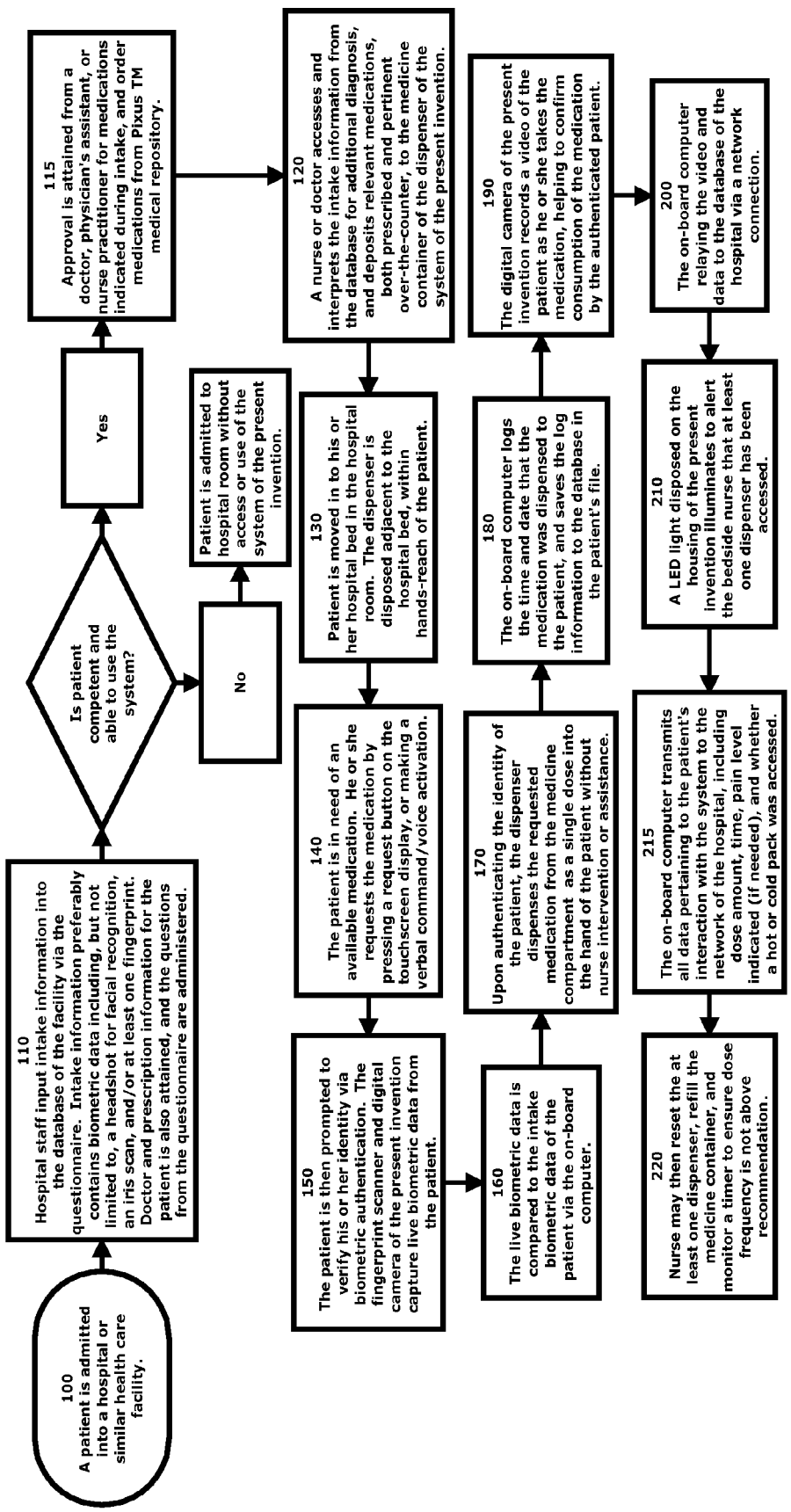
FIG. 1 is a flow chart of the process of use of the present invention.

The present invention is a medication dispensing and tracking system configured for use at the bedside of a patient. The present invention is preferably employed in hospitals and similar medical centers for patients' personal use. As such, the present invention is preferably accessible to the patient without the need to stand or get out of the bed, preventing the need to walk, and helping to avoid falls.

The present invention is preferably equipped with a touchscreen display (10), an on-board computer (15) a bed anchor (20), at least one dispenser (30), a medicine compartment (35) disposed in each iteration of the at least one dispenser (30), a biometric identity authentication system consisting of a fingerprint reader (40) and a camera (75), a mount (45) and a swivel arm (50). The on-board computer (15), at least one dispenser (30), medicine compartment (35), biometric identity authentication system and touchscreen display (10) are preferably contained within a housing (70) in communication with the swivel arm (50) which may be moved and adjusted about the mount (45). Additionally, a portion of the present invention is bolted or otherwise affixed to the patient's bed via the bed anchor (20) to prevent theft. It should be noted that the present invention is preferably mounted to the bed (bed frame or support poles) rather than the floor of the hospital room to facilitate and expedite cleaning of the hospital room between patients. It should be understood that the present invention may be removed from the bed with a proprietary key or similar tool to be used exclusively by authorized personnel.

The present invention is preferably configured to be situated at either the right or left side of the bed of the patient, and may preferably be moved easily at the request of the patient. The at least one dispenser (30) of the present invention is preferably configured to swing in front of the patient via the mount (45) and swivel arm (50), and may be adjusted up, down, left, or to the right for the convenience of the patient. The swivel arm (50) is preferably adjusted via an electric servo motor, however it is envisioned that the position of the at least one dispenser (30) may be manually adjusted via adjustment knobs.

In the preferred embodiment of the present invention, the swivel arm (50) is preferably equipped with a cup holder (55), which provides a resting place for a cup or bottle of water, or any other beverage of the patient to facilitate the patient swallowing dispensed medication. Some embodiments of the present invention are preferably equipped with a specialized cup configured to fit with the cup holder (55). Such a cup is preferably equipped with two handles, as to facilitate use of the cup by stroke victims, who may grab the cup from both sides. The cup is also equipped with an optional straw or sippy-cup top to assist in spill-free use by patients of all ages and conditions.

The system of the present invention employs a medication compartment configured to dispense an individual dose of prescribed medication or approved over-the-counter medication upon request. A patient must manually request the medication from the dispenser for the medication compartment (35) to dispense the dose. Each dose of any medications available to the patient are individually compartmentalized such that only one dose is available to the patient at a time. As such, each iteration of the at least one dispenser (30) of the present invention is equipped with a separate medication compartment (35) for housing a single dose of medication. The medication housed in each of the at least one dispenser (30) is tracked and mapped via the onboard computer (15) of the present invention.

Figure 3:
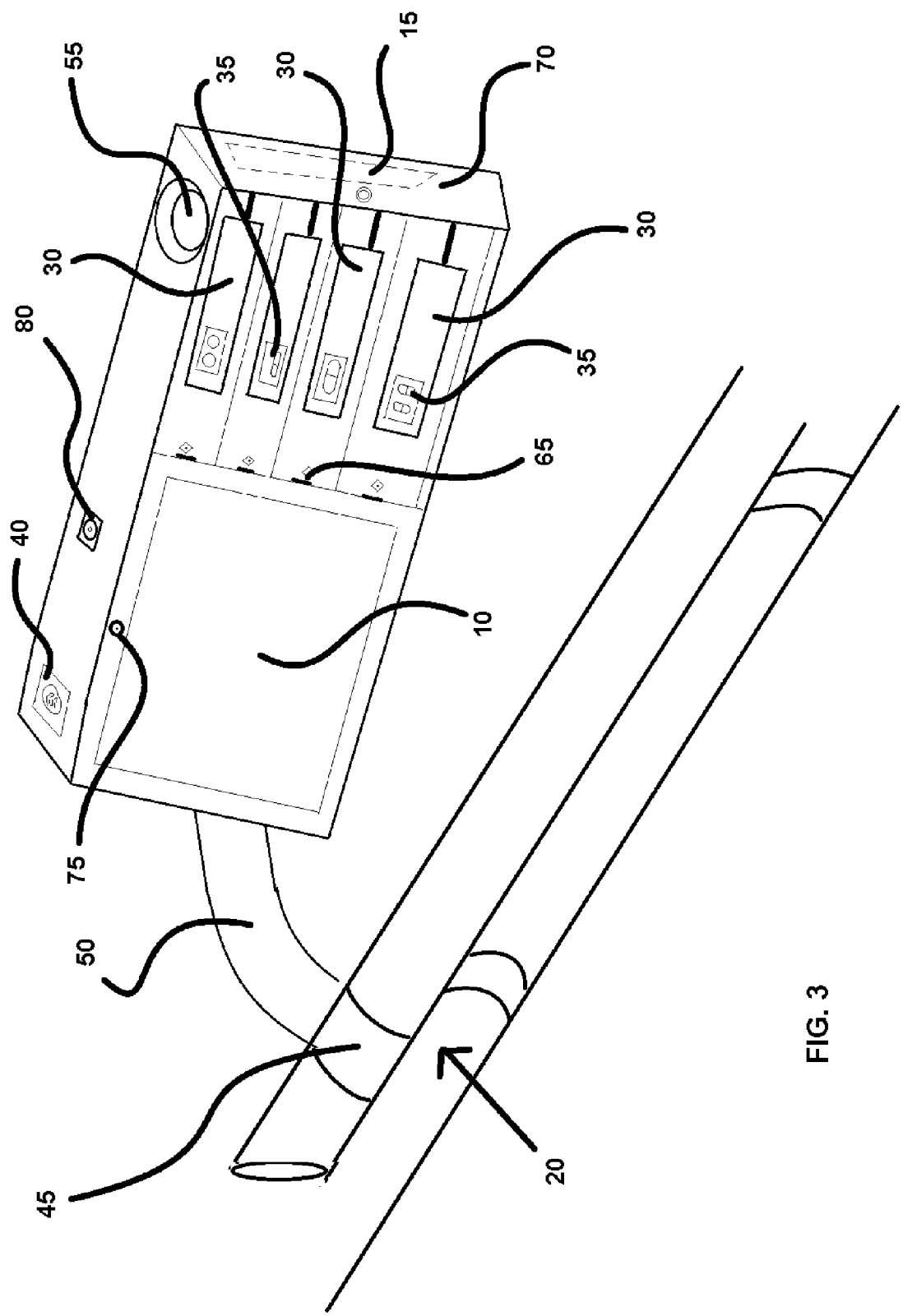
FIG. 3 displays an embodiment of the medication dispenser of the medication dispensing system of the present invention as seen from the front.

In order to successfully request medication, the identity of the patient must first be authenticated. Authentication is preferably facilitated via an onboard biometric sensor, such as an electronic fingerprint reader, iris scanner, facial recognition, voice recognition, or a hospital unique identification bracelet barcode. It is envisioned that dual biometric authentication is preferably required in order for a patient to access any iteration of the at least one dispenser (30) of the present invention. The patient preferably initiates the biometric identity authentication process by touching the touchscreen display (10), and initiating a request for medication. A request for medication via voice may also be interpreted by the on-board computer (15) in lieu of interaction with the touchscreen display (10). Upon selection of the desired available medication, and a confirmed biometric identity of the patient, the at least one dispenser (30) becomes available to the patient for use. The at least one dispenser (30) may be held behind a locked door (65) disposed near or adjacent to the touchscreen display (10) of the present invention, as shown in FIG. 3.

The system of the present invention preferably employs two steps of biometric authentication before permitting the patient access to medication dispensed from the medication compartment. An on-board computer is configured to interface with the biometric authentication equipment of the present invention to verify the identity of the patient by matching biometric data gathered from the biometric authentication equipment against known biometric data of the patient. The known biometric data of the patient is preferably housed in the patient's digital database file, which is retrieved via network communication between the on-board computer and the systems of the hospital.

The medication compartment (35) of the present invention is preferably fairly small, and is configured to hold a single dose of medication in accordance with the needs, special conditions, and prescribed dosages specific to the patient. The limitation to a single dose within each medication compartment (35) is intended to prevent any chance for an overdose. As such, the medication compartment is preferably filled prior to the patient's arrival to the hospital bed, and is preferably refilled only if needed. It is envisioned that the medicine compartment of the dispenser of the present invention is preferably filled easily by hand by a pharmacist or a nurse. The touchscreen display (10) is configured to display information pertaining to the medications contained within the at least one dispenser (30), and is preferably configured to deactivate the display when not in use to prevent patient sleep issues. Alternate embodiments of the present invention may be equipped with medicine compartments (35) that vary in size according to the size of the pill. Referring to FIG. 3, it can be seen that the medicine compartments (35) are housed within the at least one dispenser (30), which is preferably housed behind a locked door (65). The locked door (65) may be clear or semi-opaque, and is only configured to open after patient identity is confirmed via biometric authentication. Some embodiments may employ multiple locked doors, one for each instantiation of the at least one dispenser (30), further limiting the patient's access to dispensers not containing the requested medication. Other embodiments of the present invention may be equipped with a locking mechanism on the at least one dispenser (30), which limit access to the medicine compartment (35) until dual biometric authentication of the identity of the patient is attained.

The dispenser of the system of the present invention is preferably connected to a conventional AC power source, and is preferably equipped with an onboard back-up battery to facilitate use of the present invention in locales with unstable electricity, or in cases of power outage. The AC power source is configured to power the biometric authentication equipment, the onboard computer, and the medication dispensing mechanism of the present invention.

Safe use of the system of the present invention requires accurate, present information pertaining to the medications and/or treatments the patient is taking. Therefore, additional questions are preferably added to the hospital intake form required during admission to conventional medical facilities. In addition to standard intake patient information, such as personal contact information, emergency contact information, medical history information, and current prescription and medication information, each patient is preferably asked a series of questions, either by the nurse, or by the intake staff of the medical facility. An embodiment of a questionnaire (60) containing these questions is shown in FIG. 2, which may be asked verbally by a nurse, or filled out by the patient in writing (on paper or electronically) if he or she is able. It is envisioned that these questions may vary in time and practice as specific conditions require. It should be understood that the questionnaire (60) may be administered on a computer or tablet device. Some questions of the questionnaire (60), as listed in FIG. 2, are conducive to determining what should be made available to the patient via the system of the present invention. For example, questions seven and eight asks the patient if he or she smokes or uses Nicotine Replacement Therapy (NRT) solutions. If the patient indicates 'Yes,' then NRT treatment may be made available, in some cases, to the patient via a medicine container (35) of the present invention. Similarly, if the patient indicates that he or she is in pain, cold packs and/or hot packs may be provided to the patient. Such hot and/or cold packs are preferably disposed on top or in a rear compartment of the housing (70) of the present invention.

Additionally, during intake or admission to the health or medical institution, the capability of the patient to use the system of the present invention is preferably evaluated. If, when questioned and if apparent, the patient indicates that they are mentally and physically able to make his or her own decisions about taking medication. If the patient is responsible, able, and is informed on how to use the present invention, he or she will be provided use of the present invention. If not, the medicine compartments (35) preferably remain empty, and the patient is not allowed access to the system of the present invention.

The process of use of the present invention, as depicted in FIG. 1, is preferably as follows:

1. A patient is admitted into a hospital or similar health care facility. (100)
2. Hospital staff input intake information into the database of the facility via the questionnaire. Intake information preferably contains biometric data including, but not limited to, a headshot for facial recognition, an iris scan, and/or at least one fingerprint. Doctor and prescription information for the patient is also attained, and the questions from the questionnaire are administered. (110) It is preferred that more than one form of biometric data is captured from the patient. It should be noted that the questionnaire indicates whether patient is cognitively competent and physically able to operate the system of the present invention.
3. Approval is attained from a doctor, physician's assistant, or nurse practitioner for medications indicated during intake, and order medications from Pixus™ medical repository. (115)
4. A nurse accesses and interprets the intake information from the database, and deposits relevant medications, both prescribed and pertinent over-the-counter, to the medicine container of the dispenser of the system of the present invention. (120)
5. Patient is moved in to his or her hospital bed in the hospital room. The dispenser is disposed adjacent to the hospital bed, within hands-reach of the patient. (130)
6. The patient is in need of an available medication. He or she requests the medication by pressing a request button on the touchscreen display, or making a verbal command/voice activation. (140) It is envisioned that other methods of requesting or initiating the dispensing process of the present invention may also be employed.
7. The patient is then prompted to verify his or her identity via biometric authentication. The fingerprint scanner and digital camera of the present invention capture live biometric data from the patient. (150)
8. The live biometric data is compared to the intake biometric data of the patient via the on-board computer. (160)
9. Upon authenticating the identity of the patient, the dispenser dispenses the requested medication from the medicine compartment as a single dose into the hand of the patient without nurse intervention or assistance. (170) Only one dose is contained in each medicine compartment, one medicine compartment per dispenser.
10. The on-board computer logs the time and date that the medication was dispensed to the patient, and saves the log information to the database in the patient's file. (180) A red light is preferably configured to illuminate during medication dispensing and computer logging the administration of the medication.
11. The digital camera of the present invention records a video of the patient as he or she takes the medication, helping to confirm consumption of the medication by the authenticated patient. (190)
12. The on-board computer relaying the video and data to the database of the hospital via a network connection. (200) The video and data are also preferably stored locally, so that the present invention can operate independently of the network in the event of a network and/or power outage.
13. A LED light (80) disposed on the housing (70) of the present invention illuminates to alert the bedside nurse that at least one dispenser (30) has been accessed. (210)
14. The on-board computer transmits all data pertaining to the patient's interaction with the system to the network of the hospital, including dose amount, time, pain level indicated (if needed), and whether a hot or cold pack was accessed. (215)
15. Nurse may then reset the at least one dispenser, refill the medicine container, and monitor a timer to ensure dose frequency is not above recommendation. (220)

Alternate embodiments of the present invention include integrated use of medication tracking systems configured to monitor the medication dosage levels active within the patient via proprietary nanoscale intra-pill technology, such as that of Proteus Digital Health. In such embodiments, the on-board computer of the present invention is configured to communicate with the patch of the Proteus system to further monitor medication usage and efficacy in real-time.

Additionally, some embodiments of the present invention may be equipped with additional diagnostic software and/or programs configured to interact with the patient via the touchscreen display (10). For example, if a patient is in pain and is wishing to request pain medication, the on-board computer (15) may prompt the patient to provide details about the pain they are experiencing via the touchscreen display (10). A human body may be shown to the patient on the touchscreen display (10), at which time the patient may be instructed to tap the location on the body that is in pain. Then, the touchscreen display (10) preferably prompts the patient to indicate the severity of the pain on a scale of one to ten.

Additionally, the touchscreen display (10) of the present invention is preferably configured to provide feedback to the patient. For example, the touchscreen display (10) may provide encouraging statements such as, "You are doing good things to manage your pain," or, "You have some control of your situation." This form of cognitive behavioral treatment can be beneficial to the mental state of the patient, which can help him or her to feel better as well.

The medicine containers (35) of the at least one dispenser (30) of the present invention are preferably configured to hold medications including neuropathy medication (Lyrica™), migraine Triptans, anxiety medication (Ativan™), emergency medications (SLNTG), Acetaminophen, Ibuprofen, Colace, and other medications. Alternately, some embodiments of the present invention may be equipped with a more robust patient service platform. For example, more robust embodiments of the present invention may be equipped with a music player incorporated into the on-board computer to enable the user to play music in his or her hospital room. A headphone jack and/or small speaker disposed in the housing (70) of the present invention may be configured to play the music per the instruction of the patient via the touchscreen display (10). It should be understood that the on-board computer (15), touchscreen display (10) and any other electric components of the present invention are powered conventionally via AC power, however it is envisioned that the present invention is equipped with an internal battery for use of the present invention in the event of a power outage. Similarly, it should be understood that a microphone and/or speaker are preferably present within the housing (70) of the present invention to facilitate the functionality of voice commands and biometric voice recognition. Additionally, some embodiments of the present invention are configured to read a barcode or QR-code associated with the patient to help identify the patient, supplementing the biometric authentication of the present invention.

Having illustrated the present invention, it should be understood that various adjustments and versions might be implemented without venturing away from the essence of the present invention. Further, it should be understood that the present invention is not solely limited to the invention as described in the embodiments above, but further comprises any and all embodiments within the scope of this application.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The exemplary embodiment was chosen and described in order to best explain the principles of the present invention and its practical application, to thereby enable others skilled in the art to best utilize the present invention and various embodiments with various modifications as are suited to the particular use contemplated.

I claim:

1. A method for safely delivering medication to patients of a hospital without assistance comprising:
   admitting a patient to the hospital;
   administering an intake questionnaire to generate intake information;
   wherein the intake questionnaire inquires what medications the patient is currently taking;
   capturing biometric identity data from the patient via a first fingerprint reader;
   storing the biometric identity data to a database as biometric reference data;
   hospital staff interpreting the intake information;
   hospital staff depositing relevant medications into medication containers disposed within at least one medication dispenser disposed at the side of a hospital bed of the patient;
   wherein the relevant medications are determined by said hospital staff interpreting the intake information;
   wherein the at least one medication dispenser is mounted to the hospital bed;
   transporting the patient to the hospital bed;
   the patient needing medication;
   the patient requesting medication with one hand via a touch screen display;
   a second fingerprint reader capturing the fingerprint of the patient as biometric identity authentication data;
   an on-board computer comparing the biometric identity authentication data to the biometric reference data to verify the identity of the patient;
   the patient selecting the requisite available medication via the touch screen display without nurse authorization;
   a locked door protecting at least one medication dispenser unlocking without nurse interaction;
   wherein the door is disposed in the same plane as the touch screen display;
   the patient grasping the at least one medication dispenser without nurse intervention;
   the at least one medication dispenser dispensing the medication to the patient without nurse intervention; and
   the patient consuming the medication without nurse intervention.

2. The method of claim 1, wherein the door is disposed adjacent to said touch screen display.

3. The method of claim 1, further comprising:
   an LED light illuminating after medication is accessed by the patient; and
   the LED light indicating to the nurse to refill the medication compartment.

4. A method for safely delivering medication to patients of a hospital without assistance comprising:
   admitting a patient to the hospital;
   administering an intake questionnaire to generate intake information;
   capturing biometric identity data from the patient via a first camera;
   storing the biometric identity data to a database as biometric reference data;
   hospital staff interpreting the intake information;
   hospital staff depositing relevant medications into medication containers disposed within at least one medication dispenser disposed at the side of a hospital bed of the patient;
   wherein the relevant medications are determined via said hospital staff interpreting the intake information;
   transporting the patient to the hospital bed;
   the patient needing medication, the medication being a drug indicated during said 'administering an intake questionnaire to generate intake information';
   the patient requesting medication via a voice command without hospital staff intervention;
   a second camera capturing an image of the patient as biometric identity authentication data;
   an on-board computer comparing the biometric identity authentication data to the biometric reference data to verify the identity of the patient;
   the patient selecting the requisite available medication via a touch screen display without hospital staff intervention;
   a door protecting at least one medication dispenser unlocking;
   the patient grasping the at least one medication dispenser;
   the at least one medication dispenser dispensing the medication to the patient without hospital staff intervention;
   the patient consuming the medication without hospital staff observation; and
   verifying patient consumed the medication via the second camera.

5. The method of claim 4, further comprising:
attaining approval from a doctor for medications indicated during the intake questionnaire;
the doctor ordering medications from a medical repository; and
wherein said at least one medication dispenser is disposed in fixed communication with the hospital bed within hands-reach of the patient.

6. The method of claim 5, further comprising:
an LED light disposed on the housing of the at leas tone medication dispenser illuminating, alerting hospital staff that the at least one medication dispenser has been accessed.

\* \* \* \* \*